United States Patent [19]

Booras et al.

[11] Patent Number: 5,709,866
[45] Date of Patent: Jan. 20, 1998

[54] DUAL BAG MOUTH CARE PACKAGE

[75] Inventors: John Booras, Wildwood; Charles E. Young, Crystal Lake, both of Ill.

[73] Assignee: Sage Products, Inc., Crystal Lake, Ill.

[21] Appl. No.: 761,017

[22] Filed: Dec. 5, 1996

[51] Int. Cl.$^6$ .................................................. A61M 35/00
[52] U.S. Cl. ........................... 424/400; 604/3; 604/1; 604/2
[58] Field of Search ..................... 424/400; 601/1, 601/3, 4

[56] References Cited

U.S. PATENT DOCUMENTS 5,378,226  1/1995  Hanifl .................................. 604/3
5,456,361  10/1995 Walsh et al. ...................... 206/570
5,466,153  11/1995 Poindexter ........................ 433/140

*Primary Examiner*—Thurman K. Page
*Assistant Examiner*—D. Faulkner
*Attorney, Agent, or Firm*—Lee, Mann, Smith, McWilliams, Sweeney & Ohlson

[57] ABSTRACT

A mouthcare kit comprising a pair of sealed bags formed as a unitary structure. The first bag contains a swab and a frangible first pouch carrying a liquid for impregnating an absorbent head of the swab while retained within the first bag. The second bag contains a second pouch with a moisturizing liquid which can be removed from the second bag so that the moisturizing liquid can be applied to the swab.

11 Claims, 2 Drawing Sheets

DUAL BAG MOUTH CARE PACKAGE

BACKGROUND OF THE INVENTION

This invention relates to mouth care, and in particular to a dual bag system, one of which contains at least one swab and an impregnating liquid, and the other of which contains a mouth moisturizing solution.

Mouth care swabs of the nature used in the present application are designed for single use. One example of a swab is depicted in U.S. Design Pat. No. D 282,698 owned by Sage Products, Inc. of Crystal Lake, Ill. A suction-type version of that swab is depicted in U.S. Pat. No. 5,085,633, which is also owned by Sage Products, Inc. Swabs of the nature used in the present application are impregnated with a mouth care solution before treatment of a patient. In the past, swabs have been dipped in various containers of mouth care solutions before being used for oral care. U.S. Pat. No. 5,378,226, the disclosure of which is incorporated herein by reference, relates to an improvement, where a burst pouch is incorporated within a sealed bag containing one or more swabs so that the swabs can be impregnated, while still in their package, before use. This eliminates the step of physically dipping the swabs into a mouth care solution, in whatever container the solution might be retained.

Often, however, swabs are also used to apply mouth moisturizing solutions. In the past, separate swabs have been used for applying mouth moisturizing solution, and separate containers have been supplied for that purpose. However, a compact and readily accessible kit employing both a swab impregnating solution and a separate pouch of mouth moisturizing solution has heretofore been unavailable.

SUMMARY OF THE INVENTION

The invention relates to a mouth care kit which comprises a first sealed bag comprising opposite plastic sheets having a peripheral seal. At least one swab is located in the first bag, along with a frangible first pouch. The first pouch contains a first liquid and includes means for opening the pouch while sealed within the bag to release the liquid to impregnate an absorbent head of the swab. Means is also provided in the first bag for orientating the pouch proximate the absorbent head of the swab. A second sealed bag is also provided, comprising opposite plastic sheets having a peripheral seal. A second pouch is disposed within the second bag, the second pouch containing a second liquid. The first and second bags are joined as a unitary structure.

In accordance with the preferred form of the invention, means is provided for access to the first bag, that means extending across a portion of one side of the first bag. The means for access preferably comprises a line of weakening in one wall of the first bag, such as a line of perforation.

The means for orientating the first pouch proximate the absorbent head of the swab comprises means for retaining the pouch in place. That means for retaining preferably comprises a partial barrier formed in the first bag intermediate opposite ends of the bag. The partial barrier comprises a lateral seal in the bag.

The second liquid in the second pouch preferably comprises a mouth moisturizing solution. The second bag includes means for access therein extending across a portion of one side of the bag. The means for access preferably comprises a line of weakening in one wall of the bag, with the line of weakening comprising a line of perforation in the preferred form of the invention.

BRIEF DESCRIPTION OF THE DRAWINGS

The invention is described in greater detail in the following description of an example embodying the best mode of the invention, taken in conjunction with the drawing figures, in which.

DESCRIPTION OF AN EXAMPLE EMBODYING THE BEST MODE OF THE INVENTION

Figure 1:
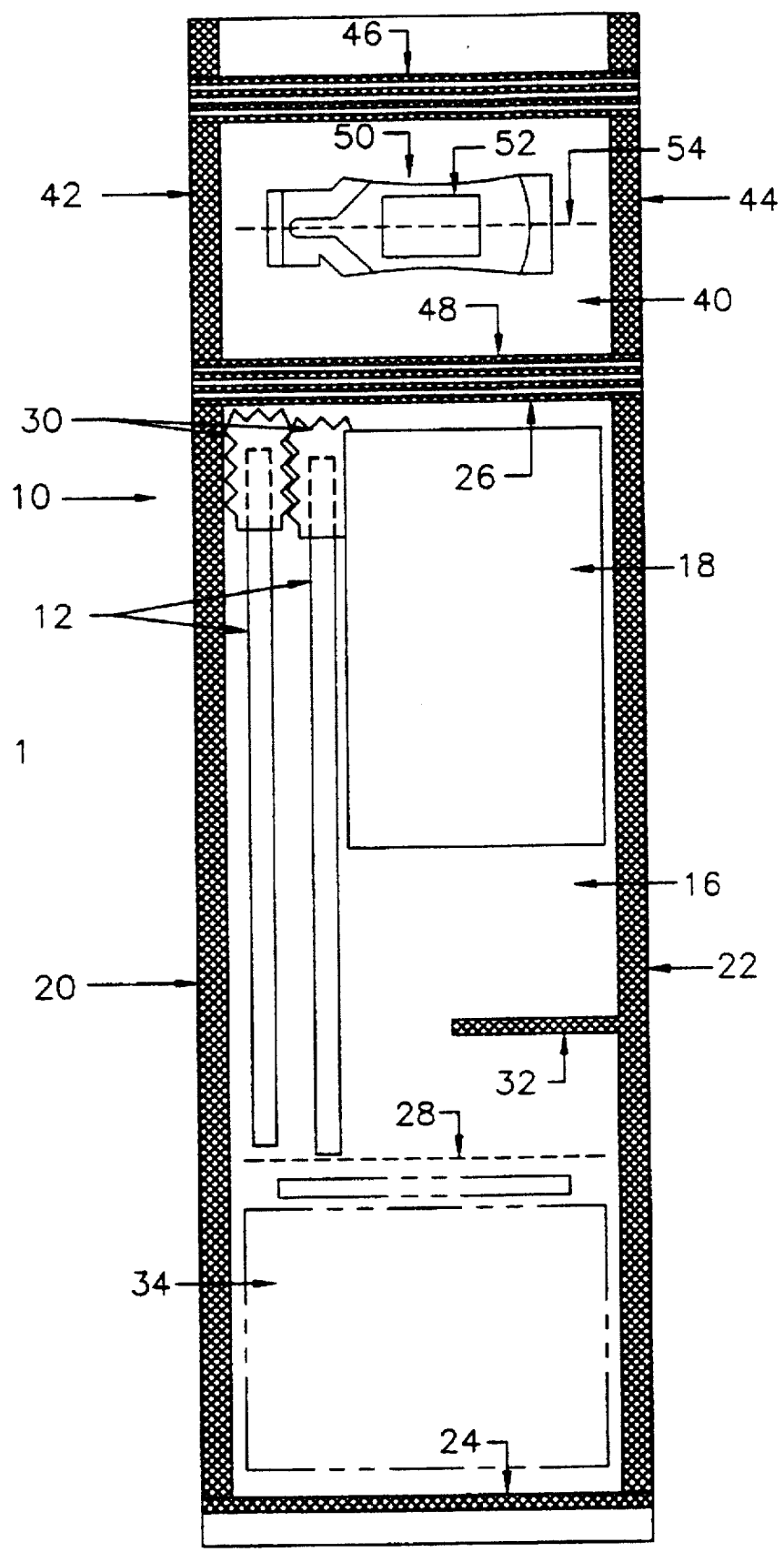
FIG. 1 is a schematic top plan view of a first form of the invention.
Figure 2:
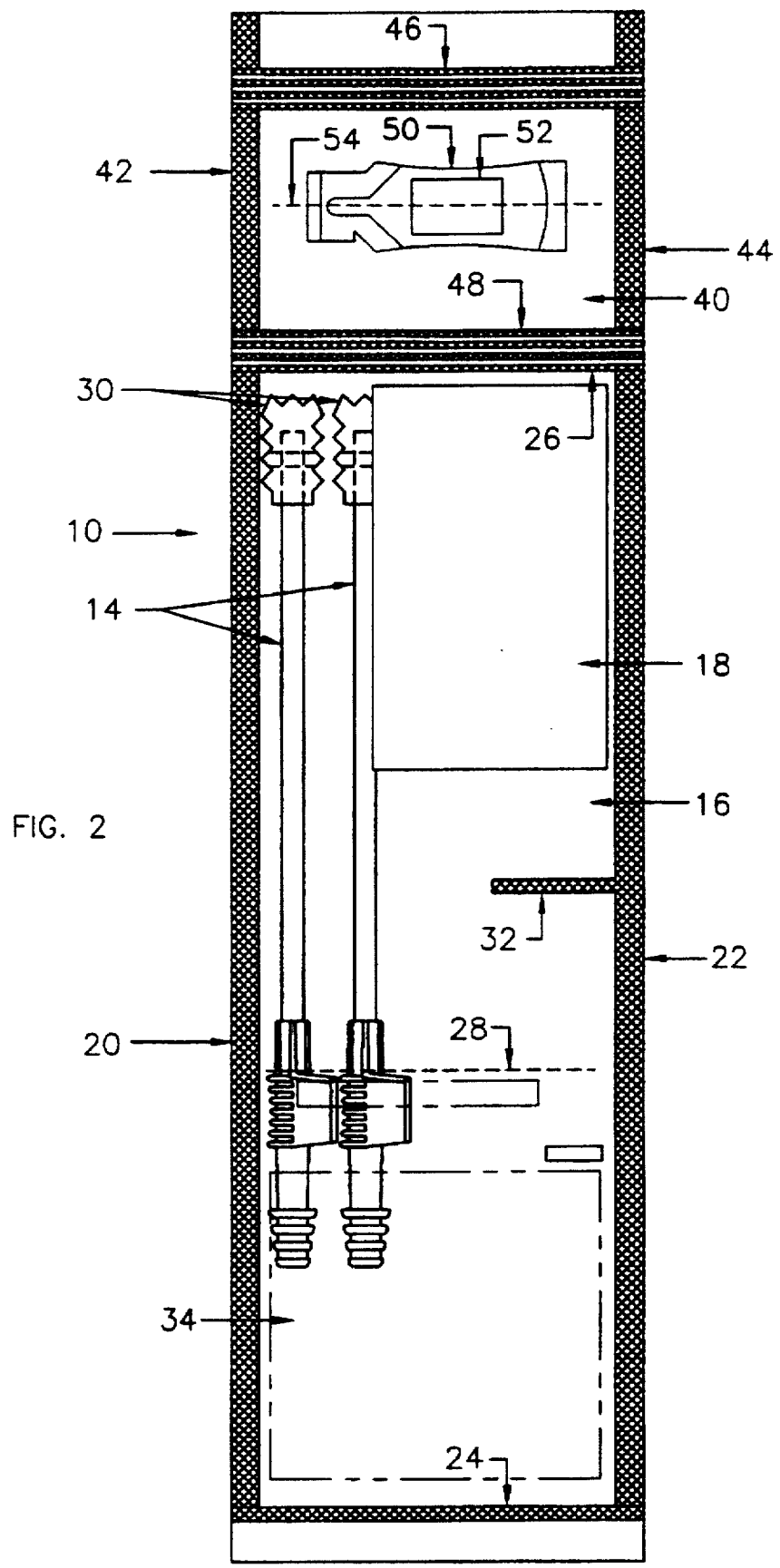
FIG. 2 is a schematic top plan view of a second form thereof.

A mouth care kit according to the invention is shown generally at 10 in the drawing figures. The only real difference between FIGS. 1 and 2 is that FIG. 1 depicts a kit containing a pair of mouth care swabs 12, while FIG. 2 depicts a kit containing a pair of suction mouth care swabs 14. Otherwise, the depicted versions of the invention are essentially the same, and will therefore not be described individually.

The swabs 12 or 14 are located within a first bag 16. Also located within the bag 16 is a burst pouch 18. The bag 16 can be formed in a conventional fashion of two sheets of plastic, such as polyethylene, which are heat sealed together at side seals 20 and 22, and at end seals 24 and 26. Alternatively, the bag 16 can be formed of a tube of polyethylene having the end seals 24 and 26. In whatever form the bag 16 is made, the swabs 12 or 14 and burst pouch 18 are located therewithin when the bag 16 is constructed.

The bag 16 also includes an access to the interior of the bag in the form of a perforation or line of weakening 28. As described and explained in greater detail in incorporated U.S. Pat. No. 5,378,226, the perforation 28 is spaced from the side edges of the bag 16 and is sized sufficiently so that the swabs 12 or 14 can be removed therefrom.

The burst pouch 18 preferably is formed of plastic, such as polyethylene, or a composite, multi-layer structure that is non-reactive to solutions contained within the pouch 18. The mouth care solution contained within the pouch 18 can be of many different forms, including a mint flavored hydrogen peroxide solution sold by Sage Products, Inc. of Crystal Lake, Ill. under the trademark "PEROX-A-MINT". The pouch 18 is formed as described in incorporated U.S. Pat. No. 5,378,226 so that the pouch 18 can be fractured within the bag 16 when desired in order to impregnate absorbent heads 30 of the swabs 12 or 14.

As explained in incorporated U.S. Pat. No. 5,378,226, it is preferred that the burst pouch 18 be retained within the bag 16 in proximity to the absorbent heads 30. To this end, the bag 16 includes a heat seal 32 extending across a portion of the bag intermediate the opposite ends of the bag. The heat seal 32 may be continuous or may be a series of spaced seals formed in the bag 16. In any form, the seal 32 is formed so that the burst pouch 18 always remains in proximity to the heads 30 and cannot migrate to the opposite end of the bag 16. Thus, when the burst pouch 18 is fractured, the solution contained there within immediately impregnates the absorbent heads 30 without the need for either re-orientating the burst pouch 18 before it is fractured, or otherwise guiding the solution therefrom to the heads 30.

The bag 16 may also include a label 34 for identifying the contents. This forms no part of the invention.

The kit also includes a second bag 36. The second bag 36 may be identical in material to the first bag 16, and indeed may be an extension thereof, with opposite side seals 42 and 44, and end seals 46 and 48.

The second bag 40 carries a second pouch 50 which is filled with a single dose of a second liquid. That liquid preferably is a mouth moisturizing solution sold under the trademark "MOIST PLUS" by Sage Products, Inc. of Crystal Lake, Ill., although other products can be incorporated, as well. The second pouch 50 may be a typical single dosage container which can be opened and applied to one or both of the absorbent heads 30 in a conventional fashion. The pouch 50 can include a label 52 thereon for identifying its contents and use.

Access to the second bag 36 is by means of a second perforation or line of weakening 54. The perforation 54 is sufficiently long so that when the bag 36 is opened there along, the pouch 50 can easily be removed. Alternatively, the perforation 54 can be omitted and the end seal 46 can be formed so that the bag 36 can be opened at that seal. A resealable seal of one kind or another can be used, as is conventional.

As illustrated in the drawing figures, the end seals 26 and 48 of the bags 16 and 40 are preferably immediately adjacent one another, and it is preferred that the seals 26 and 48 be a common seal joining the two bags 16 and 40 as a unitary structure. Alternatively, the bags 16 and 40 can be formed separately, and then joined together at the heat seals 26 and 48 to form the kit 10. Other means of formation will also be evident to one of ordinary skill in the art.

In use, before the first bag 16 is opened, the burst pouch 18 is fractured to flood and impregnate the absorbent heads 30 of the swabs 12 or 14. The swabs are then removed from the bag 16 through the perforated opening 28 and are used, or before use, the second bag 40 is opened along the perforation 54, the second pouch 50 removed therefrom, and the heads 30 impregnated with the solution within the pouch 50 before the swabs are used.

Various changes can be made to the invention without departing from the spirit thereof or scope of the following claims.

What is claimed is:

1. A mouth care kit, comprising
   a. a first sealed bag comprising opposite plastic sheets having a peripheral seal,
   b. at least one swab located in said first bag,
   c. a frangible first pouch disposed within said first bag, said first pouch containing a first liquid and including means for opening said first pouch while sealed within said first bag to release said first liquid to impregnate an absorbent head of said swab,
   d. means in said first bag for orientating said first pouch proximate said absorbent head of said swab,
   e. a second sealed bag comprising opposite plastic sheets having a peripheral seal,
   f. a second pouch disposed within said second bag, said second pouch containing a second liquid, and
   g. means joining said first and second bags as a unitary structure.

2. A mouth care kit according to claim 1 including means for access to said first bag extending across a portion of one side of said first bag.

3. A mouth care kit according to claim 2 in which said means for access comprises a line of weakening in one wall of said first bag.

4. A mouth care kit according to claim 1 in which said means for orientating comprises means for retaining said pouch proximate said absorbent head.

5. A mouth care kit according to claim 4 in which said means for retaining comprises a partial barrier formed in said first bag intermediate opposite ends thereof.

6. A mouth care kit according to claim 5 in which said partial barrier comprises a lateral seal in said first bag.

7. A mouth care kit according to claim 1 in which said second liquid comprises a mouth moisturizing solution.

8. A mouth care kit according to claim 1 in which said second bag includes means for access extending across a portion of one side of said second bag.

9. A mouth care kit according to claim 8 in which said means for access comprises a line of weakening in one wall of said first bag.

10. A mouth care kit according to claim 9 in which said line of weakening comprises a perforation.

11. A mouth care kit according to claim 1 in which said peripheral seals are heat seals.

* * * * *